US00PP08703P

United States Patent [19]

Devine

[11] Patent Number: Plant 8,703

[45] Date of Patent: Apr. 26, 1994

[54] CORNUS KOUSA VARIETY CV. PARASOL

[75] Inventor: William Devine, Kennedyville, Md.

[73] Assignee: Joseph Cesarini, Ridgely, Md.

[21] Appl. No.: 82,053

[22] Filed: Jun. 23, 1993

[51] Int. Cl.[5] ..... A01H 5/00
[52] U.S. Cl. ..... Plt./53.2
[58] Field of Search ..... Plt. 53.2

*Primary Examiner*—James R. Feyrer
*Attorney, Agent, or Firm*—Synnestvedt & Lechner

[57] ABSTRACT

A new and distinct variety of Cornus Kousa plant named "Parasol" that is particularly characterized by its branching habit resembling the spokes of an umbrella, its beautiful flower heads with numerous rounded, ivory-white bracts, and its deep red autumn foliage.

6 Drawing Sheets

BACKGROUND AND SUMMARY OF THE INVENTION

This invention relates to the discovery and asexual propagation of a new and distinct variety of Cornus Kousa, a member of the Cornaceae family, and commonly referred to as Japanese Dogwood. The new Cornus Kousa variety has been named "Parasol."

The new variety was discovered by William Devine, in the fall of 1969, as a chance seedling from an unnamed specimen of Cornus Kousa of unknown parentage, growing in the cultivated, landscaped yard of a home in Silver Spring, Montgomery County, Md. It was one of a number of seedlings resulting from open-pollinated seed collected from the Cornus Kousa yard specimen. Some of the seedlings were transplanted and grown to flowering age in a bed of a nursery in Kennedyville, Kent County, Md. A total of four seedlings were observed, two of which demonstrated poor growth habit and were thus destroyed; and two of which demonstrated quality leaf characteristics and flowering. The two retained seedlings were named "Double-one," which later became "Doubloon," and "Double-two" which, after observation of its distinctive branching characteristics, became "Parasol."

The new Cornus Kousa variety was first propagated by William Devine in the summer of 1975, when he rooted cuttings and did several field grafts on both varieties. The "Doublooon" variety was released originally for observation, but with no restriction on further propagation, and has since been released commercially. The "Parasol" variety was never released and is the subject of this invention. The original "Parasol" mother plant has been subsequently destroyed.

"Parasol" most closely resembles "Doubloon" and is considered to be most closely related to "Doubloon." The new Cornus Kousa "Parasol" variety is currently being grown in Kennedyville, Kent County, Md., and testing has shown it maintains its distinguishing characteristics, as hereinafter set out, through successive asexual propagation using both root cuttings and grafting.

The new Cornus Kousa "Parasol" variety is an excellent ornamental plant exhibiting beautiful flower heads of large, ivory-white bracts, and rich autumn coloration. The "Parasol" variety is unusual due to its increased number of floral bracts, creating a more abundant and attractive floral display. The flowers of "Parasol" have at least twice the number of floral bracts than the species-typical flowers of Cornus Kousa. The variety has never, during seventeen (17) years of observation, exhibited any reversion to typical inflorescence consistent with the four (4) bracted species Cornus Kousa.

From an ornamental standpoint, "Parasol" is, overall, a far more attractive plant than the "Doubloon" variety. "Parasol" is particularly distinguishable from "Doubloon" in that it demonstrates a branching habit of clusters of short side branches, resembling the spokes of an umbrella. This unique branching habit of the "Parasol" variety, along with its numerous flower bracts, creates a particularly decorative garden display.

The "Parasol" variety can be further distinguished from "Doubloon" by the following combination of characteristics. The flower bracts of "Parasol" are ivory-white in color (White 155 A), with rounded tips; whereas the flower bracts of "Doubloon" are pure white in color (White 155 D), with pointed tips. Also, "Parasol" flowers are about 5½ to 6½ cm. across, while "Doubloon" flowers are about 6 to 7 cm. across. Morever, the flowers of "Parasol" are longer lasting than those of "Doubloon."

The leaves of "Parasol" are moderate ovate in shape, about 3 to 4 cm. in width, and exhibit an entire leaf margin; whereas the leaves of "Doubloon" are broad ovate in shape, about 4 to 5 cm. in width, and exhibit a slightly undulate leaf margin. The summer mature leaves of "Parasol" are a deeper green (Green 135 A) than those of "Doubloon" (Green 141 A). In addition, "Parasol" exhibits far more beautiful fall foliage of a deeper, richer red coloration (Red 46 A) than that of "Doubloon" (Red 42 A).

"Parasol" is a hardy variety which appears resistant to summer drought-induced leaf scorch; and, compared to the "Doubloon" variety, the "Parasol" variety demonstrates much less susceptibility to dogwood borers.

BRIEF DESCRIPTION OF THE FIGURES

The new Cornus Kousa "Parasol" variety is illustrated in full color by the accompanying photographs, the colors shown being as true as can be reasonably obtained by conventional photographic procedures. The photographs illustrate the new "Parasol" plant as grown in 1992, in Kennedyville, Kent County, Md.

BOTANICAL DESCRIPTION OF THE PLANT

Figure 1:
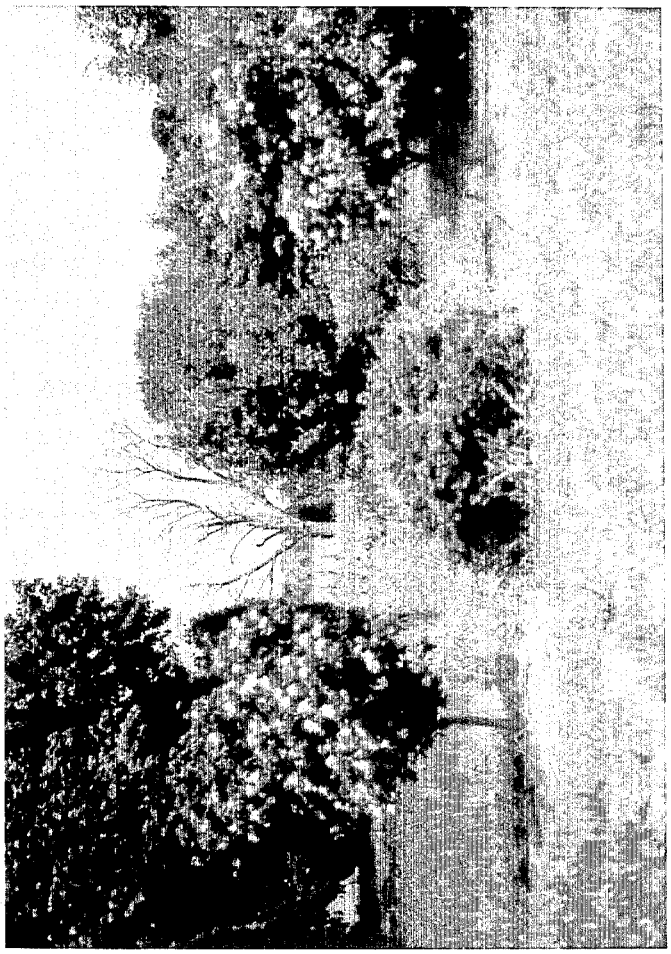
FIG. 1 is a photograph of a Cornus Kousa "Parasol" variety (left) and Cornus Kousa "Doubloon" variety (right), one week past prime flowering. The photograph illustrates the new "Parasol" variety's small, upright, oval form, as well as its dense growth habit.
Figure 2A:
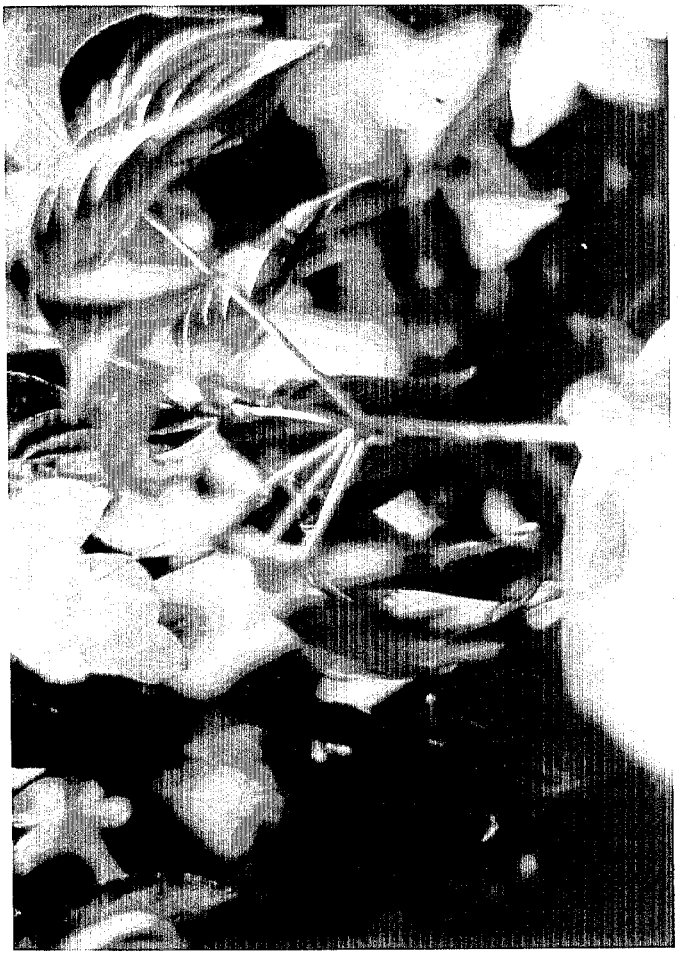
FIGS. 2*a* and 2*b* are photographs illustrating the unique branching habit of "Parasol," which particularly distinguishes "Parasol" from "Doubloon."
Figure 2B:
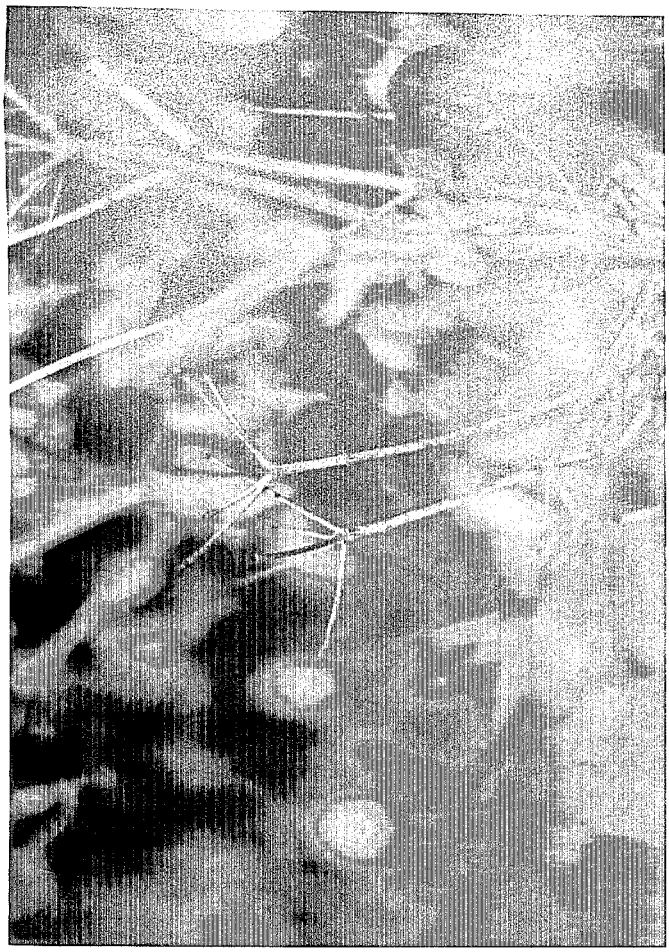
Figure 3A:
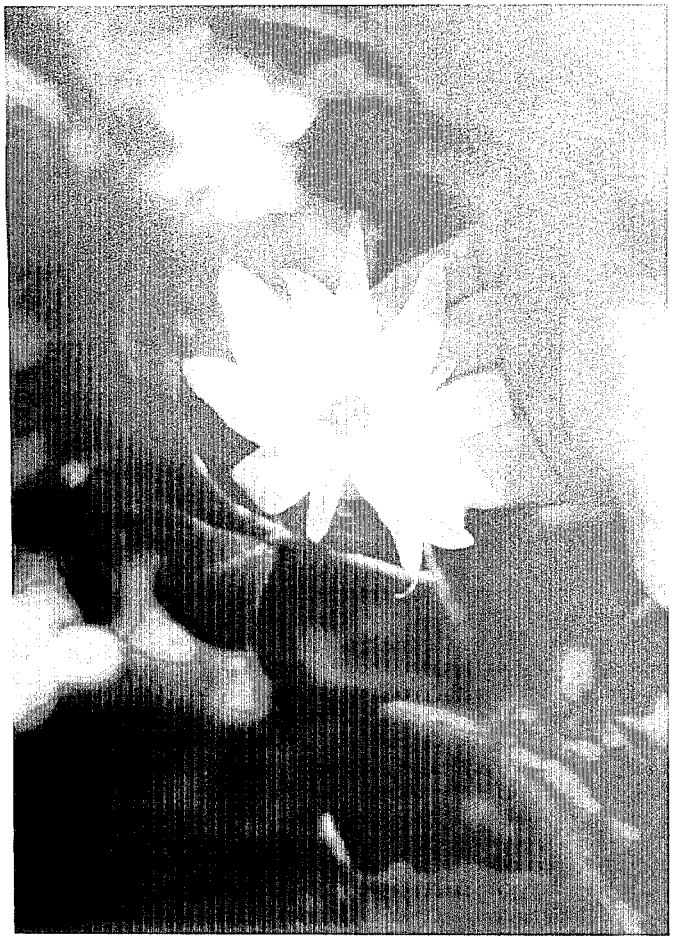
FIG. 3*a* is a photograph of a "Doubloon" variety flower, illustrating its numerous, pure white, pointed bracts; in comparison.
Figure 3B:
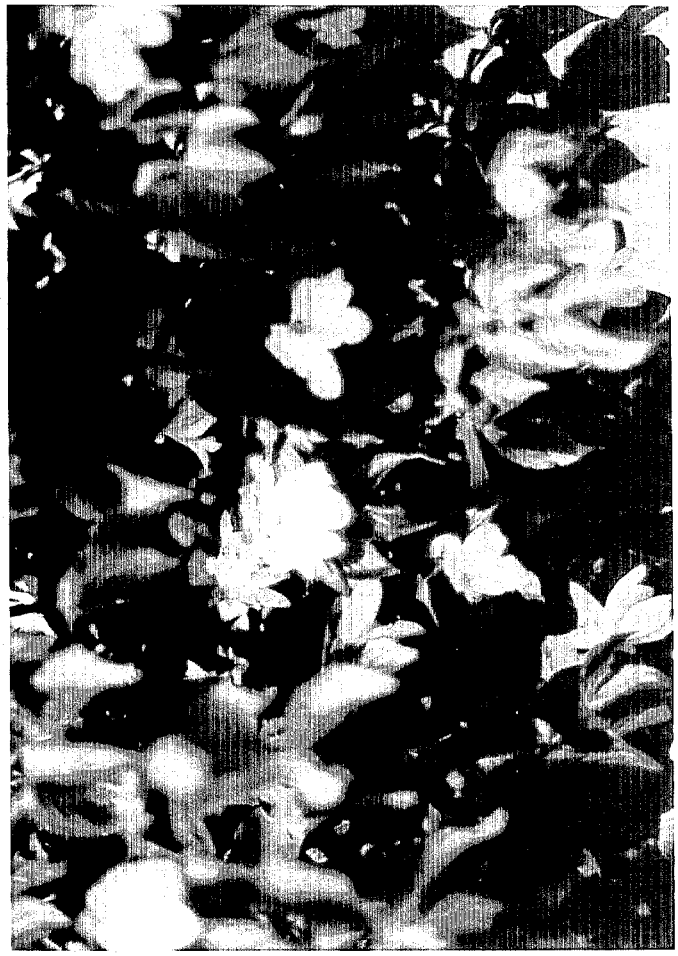
FIG. 3*b* is a photograph of a "Parasol" variety flower, illustrating its numerous bracts which are ivory-white and have rounded tips.
Figure 4:
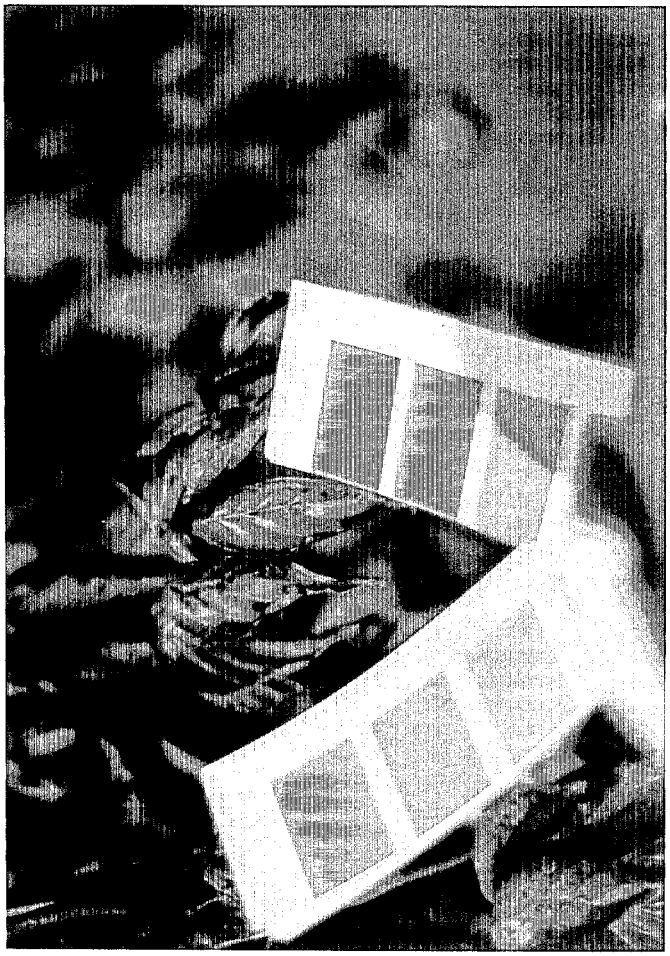
FIG. 4 is a photograph of the new "Parasol" variety's attractive fall foliage which is deeper red (Red 46 A) in color than the "Doubloon" variety (Red 42 A). This photograph also illustrates the moderate ovate shape of the "Parasol" leaves.

Throughout this specification, color names beginning with a small letter signify that the name of the color, as used in common speech, is aptly descriptive. Color names beginning with a capital letter designate values based on The R.H.S. Colour Chart published by The Royal Horticultural Society of London, England.

The following detailed description sets forth the distinctive characteristics of the new Cornus Kousa variety, "Parasol," as grown in Kennedyville, Kent County, Md., June through November, 1992, and is believed to apply to plants of the variety grown under similar conditions of soil and climate elsewhere.

Name: Cornus Kousa cv. "Parasol".

Parentage: Chance seedling from an unnamed yard specimen of Cornus Kousa, of unknown parentage.

Form: Small, upright oval form.

Growth: Dense, twiggy.

Strength: Hardy to at least about −11° F.; highly resistant to dogwood borers.

Trunk: Bark exfoliating in camouflage pattern.

*Color.*—Old bark: Greyed-green 197 C. New bark: Greyed-orange 165 B.

Branches: Most are slender, smooth; some more vigorous; stronger branches tend to terminate with characteristics clusters of fine, shorter, side branches.

*Color.*—Greyed-green 197 C.

Foliage: Dense.

Leaves:

*Size.*—About 8 to 10 cm. long×about 3 to 4 cm. wide.

*Shape.*—Moderate ovate.

*Margin.*—Entire leaf margin.

*Color.*—Summer mature: Green 135 A. Autumn: Red 46 A.

*Petiole.*—Short.

Flowers:

*Size.*—about 5½ to 6½ cm. across.

*Permanence.*—Long lasting.

*Buds.*—Rounded; about 4 to 5 mm.; bracts not fully enclosing flower buds.

*Bracts.*—Shape: Rounded tips. Size: About 2½ to 3 cm. in length. Count: Variable, from about 7 to 12 per inflorescence drooping. Color: White 155 A.

*Date of first, full flowering.*—Late May to Early June.

Fruit:

*Shape.*—Flattened globose; slightly irregular.

*Size.*—Averaging about 2 to 2½ cm. across.

*Color.*—Green at first, becoming red at maturity (consistent with the Cornus Kousa species); dropping at maturity.

I claim:

1. A new and distinct variety of Cornus Kousa plant named "Parasol" as herein illustrated and described.

* * * * *